United States Patent [19]
Sorensen

[11] Patent Number: 6,150,127
[45] Date of Patent: Nov. 21, 2000

[54] CAUSING A DESIRABLE CHANGE IN A BEHAVIOR PATTERN

[75] Inventor: Jens Ole Sorensen, Grand Cayman, Cayman Islands

[73] Assignee: Universal Ventures, Cayman Islands

[21] Appl. No.: 09/451,403

[22] Filed: Nov. 30, 1999

[51] Int. Cl.[7] .............................. C12Q 1/02; C12Q 1/04; C12Q 1/00

[52] U.S. Cl. .................................. 435/29; 435/34; 435/4

[58] Field of Search ..................... 435/29, 34, 4

[56] References Cited

U.S. PATENT DOCUMENTS 5,843,698 12/1998 Sorensen .................................. 435/29

OTHER PUBLICATIONS

Washington, "Infection Connection", Psychology Today. Jul./Aug. 1999 pp 43–44, 74, 76, 78.

"Can a Virus Make You Fat?", Discover, Apr. 1999 p. 99.

*Primary Examiner*—Louise N. Leary
*Attorney, Agent, or Firm*—Edward W. Callan

[57] ABSTRACT

A carrier-member of a test species, or a component separated from a culture thereof, that may cause a desirable change in a behavior pattern of at least one member of an adjoiner species from an initial behavior pattern to a desired behavior pattern is identified by introducing a member of a test species that is a symbiont of the adjoiner species or a component separated from a culture of the symbiont test species to at least one member of the adjoiner species that has the initial behavior pattern; and subsequently collecting data that indicates whether or not the at least one member of the adjoiner species has acquired the desired behavior pattern to thereby make said identification.

A method of causing a desirable change in a behavior pattern of a subject member of an adjoiner species from an initial behavior pattern to a desired behavior pattern, includes the step of introducing to the subject member of the adjoiner species (1) a product including an ingredient that includes, is based upon, is derived from, or is equivalent to a carrier-member of a test species that is a symbiont of the adjoiner species and has been identified as possibly causing the desirable change in the behavior pattern of some members of the adjoiner species, or (2) a product including an ingredient that includes, is based upon, is derived from, or is equivalent to at least one component separated from a culture of a carrier-member of a test species that is a symbiont of the adjoiner species, wherein the at least one component has been identified as possibly causing the desirable change in the behavior pattern of some members of the adjoiner species.

32 Claims, 4 Drawing Sheets

CAUSING A DESIRABLE CHANGE IN A BEHAVIOR PATTERN

BACKGROUND OF THE INVENTION

The present invention is directed to causing a desirable change in a behavior pattern from an initial behavior pattern to a desired behavior pattern.

As used herein the term "behavior pattern" relates to activities that are mental-based or psychological-based, such as compulsive behavior. Behavior patterns that one may desire to change include, but are not limited to, overeating, bulimia, addictive smoking, alcoholism, drug addiction, sexual-activity-related addictions, gambling addiction, grinding teeth, depression, panic attacks, fright neurosis, anger-driven conduct, daredevil risk taking and pyromania.

SUMMARY OF THE INVENTION

The present invention provides a method of identifying a carrier-member of a test species that may cause a desirable change in a behavior pattern of at least one member of an adjoiner species from an initial behavior pattern to a desired behavior pattern, the method comprising the steps of:

(a) providing either (i) a sample member of a test species that is a symbiont of the adjoiner species, or (ii) a culture of the symbiont test species;

(b) introducing the sample member of the test species, or the culture thereof, to at least one member of the adjoiner species that has the initial behavior pattern; and subsequently (c) collecting data that indicates whether or not the at least one member of the adjoiner species has acquired the desired behavior pattern to thereby make said identification.

Another aspect of the present invention provides a method of identifying a carrier-member of a test species that may cause a desirable change in a behavior pattern of at least one member of an adjoiner species from an initial behavior pattern to a desired behavior pattern, the method comprising the steps of:

(a) providing a sample member of a test species that is a symbiont of the adjoiner species;

(b) preparing a culture from said sample member of the test species;

(c) separating the culture into a plurality of components;

(d) introducing at least one of the separated components to at least one member of an adjoiner species that has the initial behavior pattern; and subsequently (e) collecting data that indicates whether or not the at least one member of the adjoiner species has acquired the desired behavior pattern to thereby make said identification.

A further aspect of the present invention provides a method of identifying a component of a carrier-member of a test species that is a symbiont of an adjoiner species and has been identified as possibly causing a desirable change in a behavior pattern of at least one member of the adjoiner species from an initial behavior pattern to a desired behavior pattern, the method comprising the steps of:

(a) providing either (i) a sample of the identified carrier-member of the test species or (ii) a culture of the identified carrier-member of the test species;

(b) separating the identified carrier-member of the test species or the culture thereof into a plurality of components;

(c) introducing at least one of the separated components to at least one member of an adjoiner species that has the initial behavior pattern; and subsequently (d) collecting data that indicates that the at least one member of the adjoiner species has acquired the desired behavior pattern to thereby make said component identification.

The present invention also provides a method of causing a desirable change in a behavior pattern of a subject member of an adjoiner species from an initial behavior pattern to a desired behavior pattern, the method comprising the step of:

(a) introducing to the subject member of the adjoiner species a product including an ingredient that includes, is based upon, is derived from, or is equivalent to a carrier-member of a test species that is a symbiont of the adjoiner species and has been identified as possibly causing the desirable change in the behavior pattern of some members of the adjoiner species.

In another aspect, the present invention provides a method of causing a desirable change in a behavior pattern of a subject member of an adjoiner species from an initial behavior pattern to a desired behavior pattern, wherein the method comprising the step of:

(b) introducing to the subject member of the adjoiner species a product including an ingredient that includes, is based upon, is derived from, or is equivalent to at least one component separated from a culture of a carrier-member of a test species that is a symbiont of the adjoiner species, wherein the at least one component has been identified as possibly causing the desirable change in the behavior pattern of some members of the adjoiner species.

The present invention further provides such products and the processes for making such products.

Additional features of the present invention are described with reference to the detailed description of the preferred embodiments.

DETAILED DESCRIPTION

Figure 1:
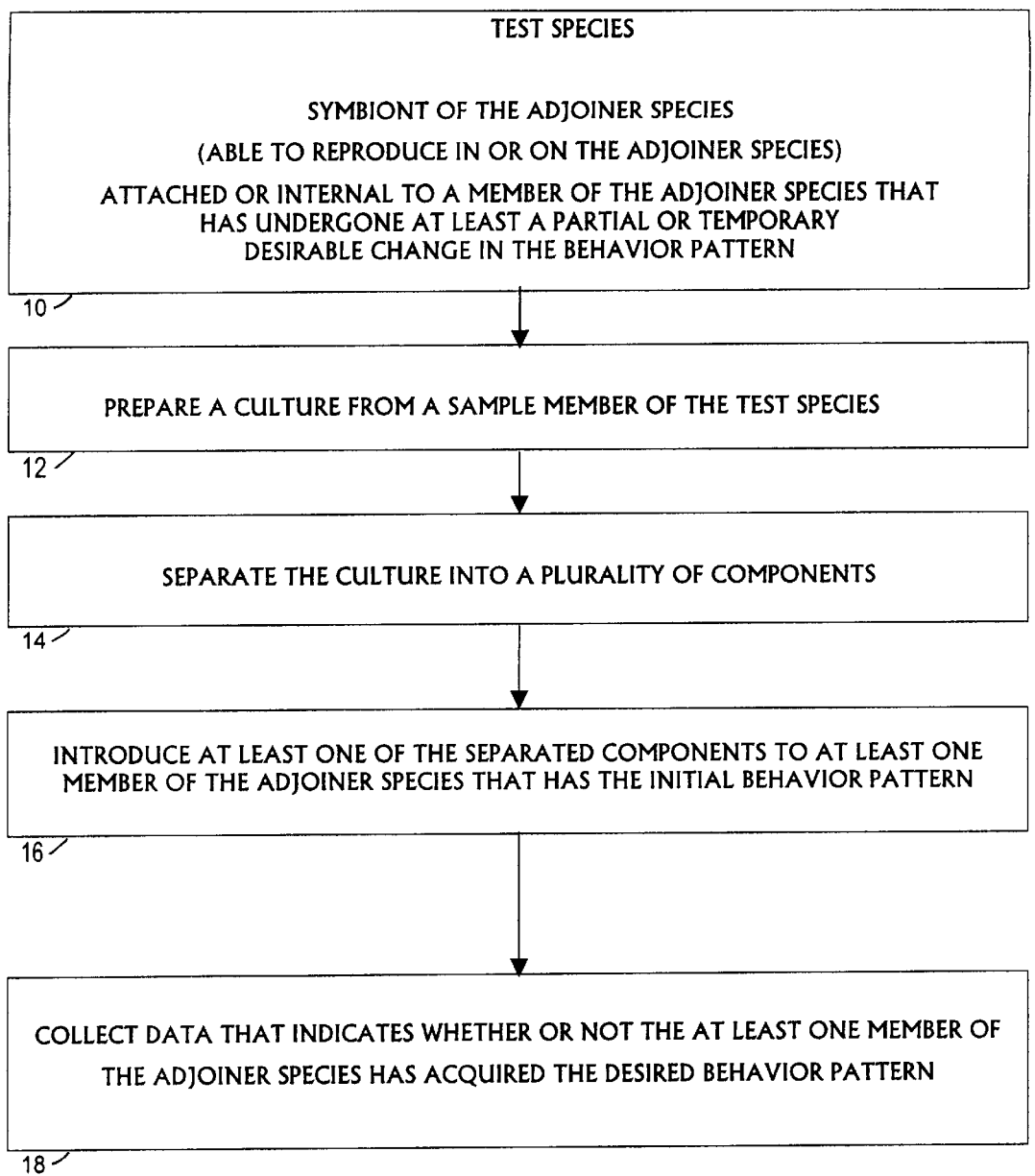
FIG. 1 is block diagram of one preferred embodiment of an identification method according to the present invention.

Referring to FIG. 1, one preferred embodiment of the method of identifying a carrier-member of a test species that may cause a desirable change in a behavior pattern of at least one member of an adjoiner species from an initial behavior pattern to a desired behavior pattern, includes a step 10 of providing a sample member of a test species that is a symbiont of the adjoiner species, a step 12 of preparing a culture from the sample member of the test species, a step 14 of separating the culture into a plurality of components; a step 16 of introducing at least one of the separated components to at least one member of the adjoiner species that has the initial behavior pattern; and subsequently a step 18 of collecting data that indicates whether or not the at least one member of the adjoiner species has acquired the desired behavior pattern to thereby make said identification.

In some embodiments of the methods described with reference to FIGS. 1, 2 and 3 the symbiont test species is able to reproduce in or on the adjoiner species.

In the embodiment described with reference to FIG. 1, the sample-member-providing step 10 may include the step of identifying the test species as a symbiont of the adjoiner species when the test species had not been known to be a symbiont of the adjoiner species.

In the embodiment described with reference to FIG. 1, it is preferable to execute the sample-member-providing step 10 and the component-introduction step 16 methodically and systematically with a large number of the selected test species and to execute the component-introduction step 16 methodically and systematically with a large number of members of the adjoiner species that have the initial behavior pattern.

Figure 2:
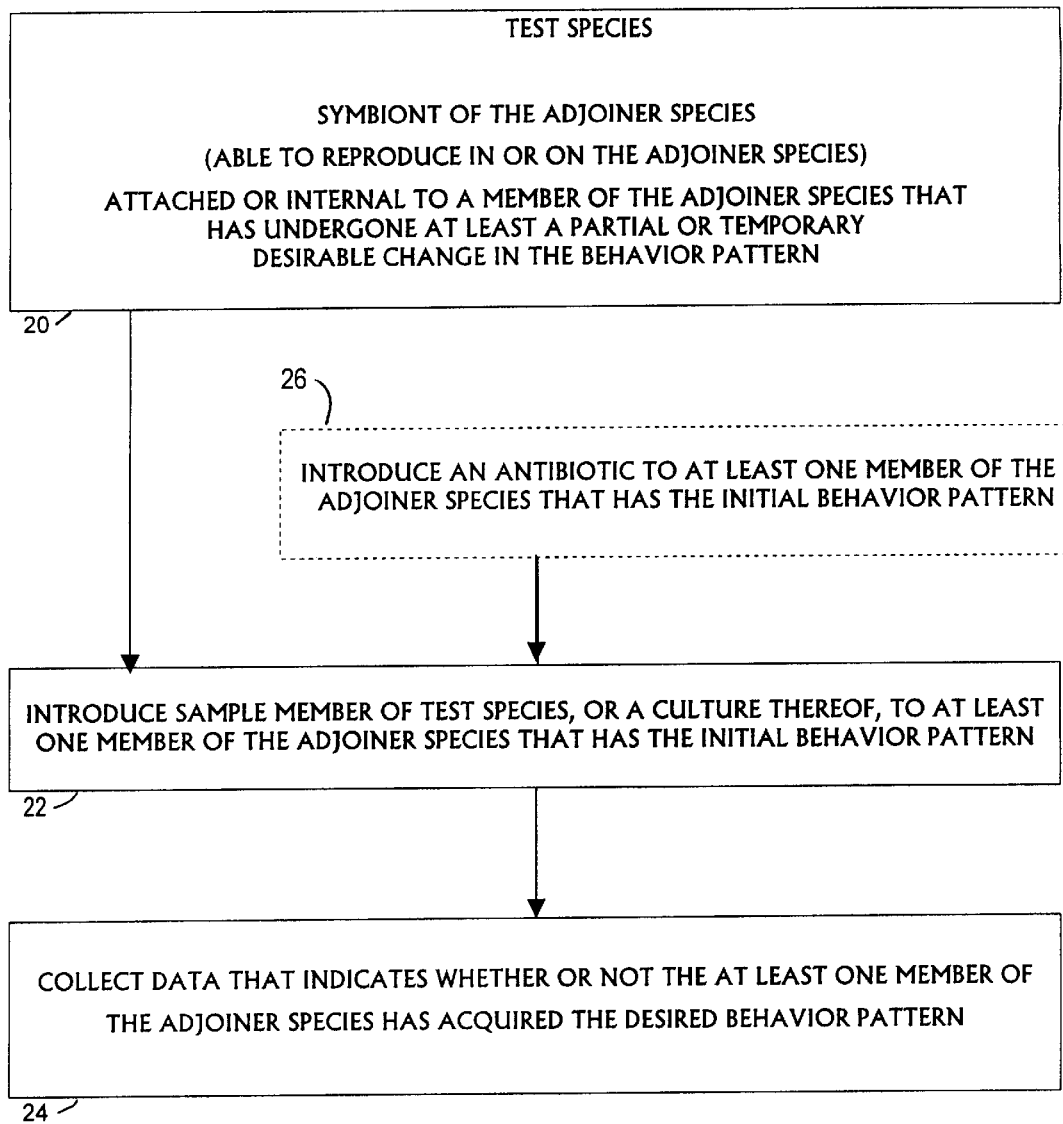
FIG. 2 is block diagram of another preferred embodiment of an identification method according to the present invention.

Referring to FIG. 2, another preferred embodiment of the method of identifying a carrier-member of a test species that may cause a desirable change in a behavior pattern of at least one member of an adjoiner species from an initial behavior pattern to a desired behavior pattern, includes a step 20 of providing either (i) a sample member of a test species that is a symbiont of the adjoiner species, or (ii) a culture of the symbiont test species; a step 22 of introducing the sample member of the test species, or the culture thereof, to at least one member of the adjoiner species that has the initial behavior pattern; and subsequently a step 24 of collecting data that indicates whether or not the at least one member of the adjoiner species has acquired the desired behavior pattern to thereby make said identification.

In alternative embodiments, the culture of the symbiont test species introduced to the member of the adjoiner species during step 22 is either a live culture or a dead culture. In some live-culture embodiments involving a symbiont test species that is able to reproduce in or on the adjoiner species, the culture is weakened in order to prevent such reproduction.

The alternative embodiments in which a live member of the symbiont test species or a culture thereof is introduced to the member of the adjoiner species during step 22 may further include a step 26 prior to step 22 of introducing an antibiotic to the at least one member of the adjoiner species that has the initial behavior pattern to thereby eliminate from the at least one member of the adjoiner species organisims that may inhibit the at least one member of the adjoiner species from acquiring the desired behavior pattern in response to the live member(s) of the test species introduced to the least one member of the adjoiner species during step 22.

When a live member of the symbiont test species is introduced to the member of the adjoiner species during step 22 it may be necessary to introduce an antibiotic to the at least one member of the adjoiner species subsequent to the step 22 if the at least one member of the adjoiner species experiences a pathological event following the introduction of the live member of the test species during step 22.

In the embodiments described with reference to FIG. 2, it is preferable to execute the sample-member-providing step 20 and the component-introduction step 22 methodically and systematically with a large number of the selected test species and to execute the component-introduction step 22 methodically and systematically with a large number of members of the adjoiner species that have the initial behavior pattern.

In some embodiments of the method described with reference to FIG. 2, the sample-member-providing step 20 may include the step of identifying the test species as a symbiont of the adjoiner species when the test species had not been known to be a symbiont of the adjoiner species.

Figure 3:
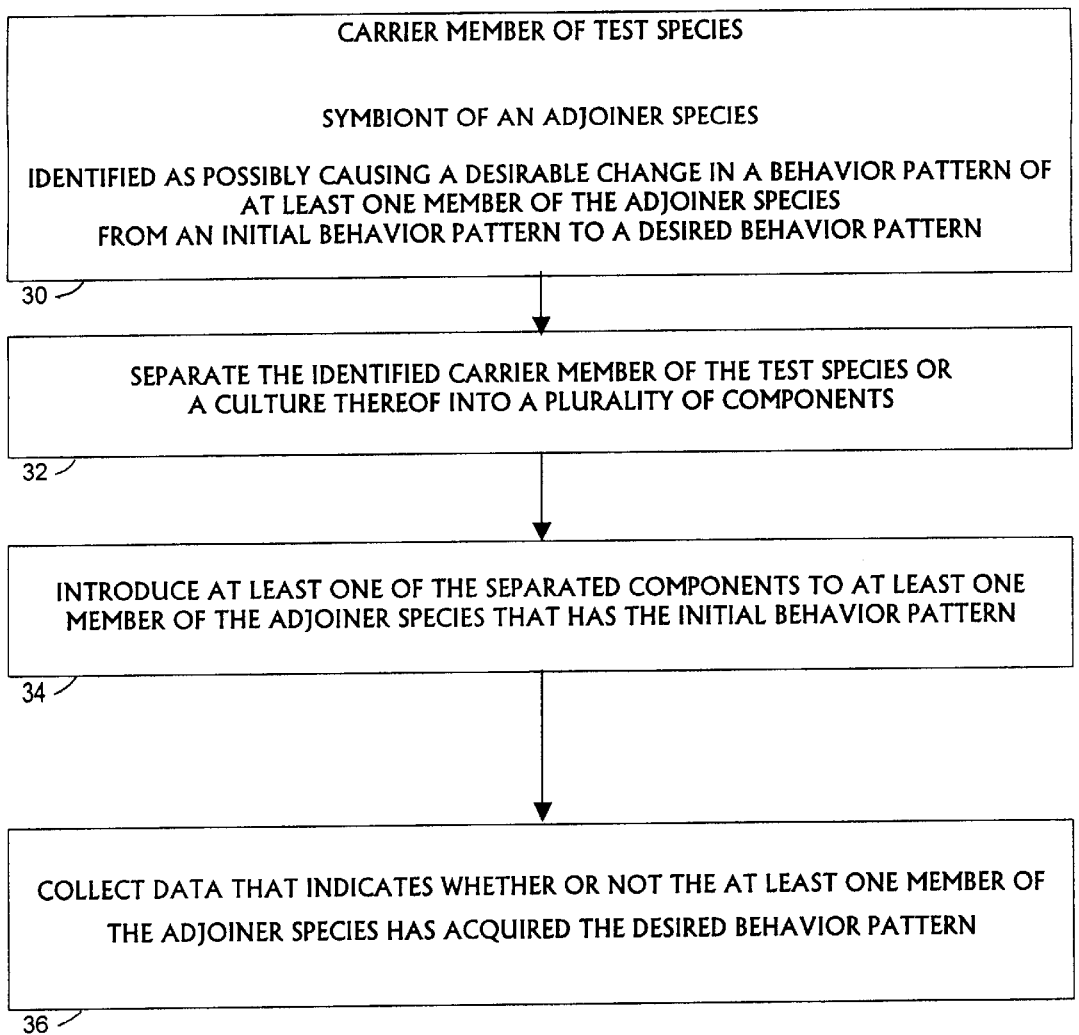
FIG. 3 is block diagram of still another preferred embodiment of an identification method according to the present invention.

Referring to FIG. 3, a preferred embodiment of a method of identifying a component of a carrier-member of a test species that is a symbiont of an adjoiner species and has been identified as possibly causing a desirable change in a behavior pattern of at least one member of the adjoiner species from an initial behavior pattern to a desired behavior pattern, includes a step 30 of providing either (i) a sample of the identified carrier-member of the test species or (ii) a culture of the identified carrier-member of the test species, a step 32 of separating the identified carrier-member of the test species or the culture thereof into a plurality of components, a step 34 of introducing at least one of the separated components to at least one member of an adjoiner species that has the initial behavior pattern; and subsequently a step 36 of collecting data that indicates whether or not the at least one member of the adjoiner species has acquired the desired behavior pattern to thereby make said identification.

In the embodiments described with reference to FIG. 3 it is preferable to execute the preparing step 30 and the component-introduction step 34 methodically and systematically with a large number of the identified test species and to execute the component-introduction step 34 methodically and systematically with a large number of members of the adjoiner species that have the initial behavior pattern.

In the various embodiments of the identification methods described herein, the adjoiner species include, but are not limited to, the human species and a species having a near-human-species genetic composition, such as chimpanzees and pigs.

In the various embodiments of the identification methods described herein, the test species are selected from among test species that are or were attached or internal to a member of the adjoiner species that has undergone the desirable change in the behavior pattern. The desirable change in the behavior pattern may be temporary or partial, such a reduction in the frequency or intensity of the undesired behavior. Samples of the selected test species are collected from either a member of the adjoiner species that has the undergone the desirable change in the behavior pattern, or from a member of the adjoiner species having the initial behavior pattern prior to the component-introduction step 16 that preceded the desirable change in the behavior pattern. In the various embodiments of the identification methods described herein, the test species include, but are not limited to, those species listed below in Table A.

TABLE A

| | |
|---|---|
| Demodex folliculorum | Mycobacterium leprae |
| Lactobacillus acidophilus | Mycobacterium bovis |
| Lactobacillus rhamnosus | Rickettsia typhi |
| Lactobacillus bulgaricus | Entamoeba histolitica |
| Lactobacillus Plantarum | Giardia lamblia |
| Streptococcus faecium | Toxoplasma gondii |
| Streptococcus thermophilus | Ascaris lumbricoides |
| Bifudus adolescentis | Trichinella spiralis |
| Bifidus longum | Histoplasma capsulatum |
| Treponema pallidum | Coccidioides immitis |

TABLE A-continued

| | |
|---|---|
| Borrelia burgdorferi | Candida albicans |
| Strepobacillus moniliformis | Picornavirusses |
| Bacteroides fragilis | Herpes simplex |
| Clostridium tetani | Chlamydia psittaci |
| Actinomyces iraelii | Mycoplasma pneumoniae |

Figure 4:
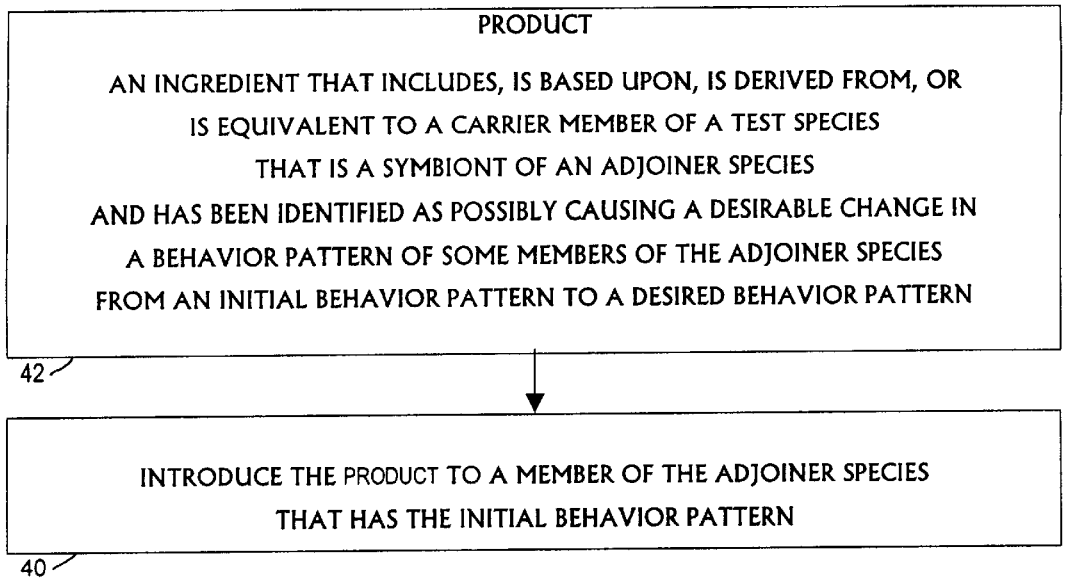
FIG. 4 is block diagram of one preferred embodiment of a method of causing a desirable change in a behavior pattern according to the present invention.

Referring to FIG. 4, one preferred embodiment of a method of causing a desirable change in a behavior pattern of a subject member of an adjoiner species from an initial behavior pattern to a desired behavior pattern includes the step of 40 introducing to the subject member of the adjoiner species a product 42 including an ingredient that includes, is based upon, is derived from, or is equivalent to a carrier-member of a test species that is a symbiont of the adjoiner species and has been identified as possibly causing the desirable change in the behavior pattern of some members of the adjoiner species. Such identification may have been accomplished by the identification method described herein with reference to FIG. 2 or by some other technique.

When a live member of a test species or a culture thereof is included in the product, the method of FIG. 4 may further include prior to the product-introduction step 40, a step of introducing an antibiotic to the subject member of the adjoiner species, to thereby eliminate from the at least one member of the adjoiner species any organisms that may inhibit the at least one member of the adjoiner species from acquiring the desired behavior pattern in response to the live member(s) of the test species introduced to the least one member of the adjoiner species during step 40.

A process for making the product described above with reference to FIG. 4 includes the step of including within the product the above-described ingredient that includes, is based upon, is derived from, or is equivalent to a carrier-member of a test species that is a symbiont of the adjoiner species and has been identified as possibly causing the desirable change in the behavior pattern of some members of the adjoiner species.

Figure 5:
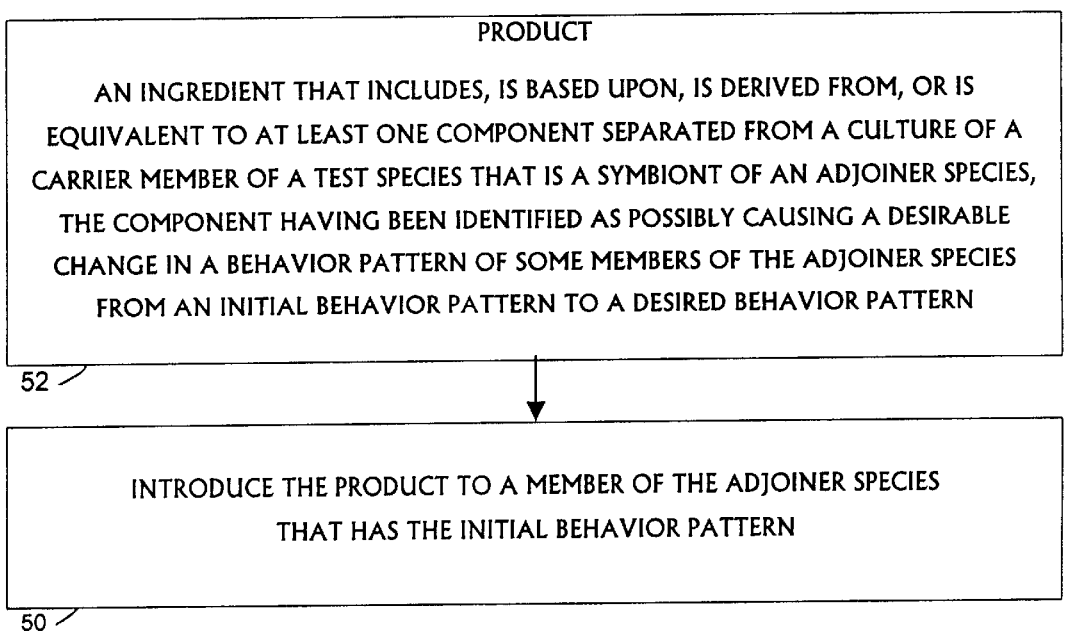
FIG. 5 is block diagram of another preferred embodiment of a method of causing a desirable change in a behavior pattern according to the present invention.

Referring to FIG. 5, another preferred embodiment of a method of causing a desirable change in a behavior pattern of a subject member of an adjoiner species from an initial behavior pattern to a desired behavior pattern includes step 50 of introducing to the subject member of the adjoiner species a product including an ingredient that includes, is based upon, is derived from, or is equivalent to at least one component separated from a culture of a carrier-member of a test species that is a symbiont of the adjoiner species, wherein the at least one component has been identified as possibly causing the desirable change in the behavior pattern of some members of the adjoiner species. Such identification may have been accomplished by the identification method described herein with reference to FIGS. 1 or 3 or by some other technique.

A process for making the product described above with reference to FIG. 5 includes the step of including within said product an ingredient that includes, is based upon, is derived from, or is equivalent to at least one component separated from a culture of a carrier-member of a test species that is a symbiont of the adjoiner species, wherein the at least one component has been identified as possibly causing the desirable change in the behavior pattern of some members of the adjoiner species.

In the various embodiments described herein, introduction to an adjoiner species member of a test species member, a culture thereof, or a component separated from a culture thereof, or a product for causing a desirable change in a behavior pattern is made orally, by topical application to an exposed body part or by injection. The injection may be topical or into the blood stream.

The advantages specifically stated herein do not necessarily apply to every conceivable embodiment of the present invention. Further, such stated advantages of the present invention are only examples and should not be construed as the only advantages of the present invention.

While the above description contains much specificity, this should not be construed as limitations on the scope of the present invention, but rather as examples of the preferred embodiments described herein. Other variations are possible and the scope of the present invention should be determined not by the embodiments described herein but rather by the claims and their legal equivalents.

I claim:

1. A method of identifying a carrier-member of a test species that may cause a desirable change in a behavior pattern of at least one member of an adjoiner species from an initial behavior pattern to a desired behavior pattern, the method comprising the steps of:

(a) providing either (i) a sample member of a test species that is a symbiont of the adjoiner species, or (ii) a culture of the symbiont test species;

(b) introducing the sample member of the test species, or the culture thereof, to at least one member of the adjoiner species that has the initial behavior pattern; and subsequently;

(c) collecting data that indicates whether or not the at least one member of the adjoiner species has acquired the desired behavior pattern to thereby make said identification.

2. A method according to claim 1, wherein steps (a) and (b) are executed methodically and systematically with a large number of said test species.

3. A method according to claim 2, wherein step (b) is executed methodically and systematically with a large number of members of the adjoiner species.

4. A method according to claim 1, wherein step (b) is executed methodically and systematically with a large number of members of the adjoiner species.

5. A method according to claim 1, 2 or 4, wherein step (a) comprises the step of:

(d) preparing a culture from said sample member of the test species; and wherein step (b) comprises the step of:

(e) introducing some of the culture of the test species to the at least one member of the adjoiner species.

6. A method according to claim 1, 2 or 4, wherein step (a) comprises the step of:

(d) selecting the test species from among test species that are or were attached or internal to a member of the adjoiner species that has undergone said desirable change in the behavior pattern.

7. A method according to claim 1, 2 or 4, wherein step (a) comprises the step of:

(d) selecting the test species from among test species that are or were attached or internal to a member of the adjoiner species that has undergone at least a partial desirable change in the behavior pattern.

8. A method according to claim 1, 2 or 4, wherein step (a) comprises the step of:

(d) selecting the test species from among test species that are or were attached or internal to a member of the adjoiner species that has undergone at least a temporary desirable change in the behavior pattern.

9. A method according to claim 1, 2 or 4, further comprising prior to step (b) the step of:

(d) introducing an antibiotic to the at least one member of the adjoiner species.

10. A method according to claim 1, 2 or 4, wherein the adjoiner species is the human species.

11. A method according to claim 1, 2 or 4, wherein the adjoiner species has a near-human species genetic composition.

12. A method according to claim 1, 2 or 4, wherein the test species is able to reproduce in or on the adjoiner species.

13. A method according to claim 1, 2 or 4, further comprising prior to step (a) the step of:

(d) identifying the test species as a symbiont of the adjoiner species when the test species had not been known to be a symbiont of the adjoiner species.

14. A method of identifying a carrier-member of a test species that may cause a desirable change in a behavior pattern of at least one member of an adjoiner species from an initial behavior pattern to a desired behavior pattern, the method comprising the steps of:

(a) providing a sample member of a test species that is a symbiont of the adjoiner species;

(b) preparing a culture from said sample member of the test species;

(c) separating the culture into a plurality of components;

(d) introducing at least one of the separated components to at least one member of an adjoiner species that has the initial behavior pattern; and subsequently (e) collecting data that indicates whether or not the at least one member of the adjoiner species has acquired the desired behavior pattern to thereby make said identification.

15. A method according to claim 14, wherein steps (a) and (d) are executed methodically and systematically with a large number of said test species.

16. A method according to claim 15, wherein step (d) is executed methodically and systematically with a large number of members of the adjoiner species.

17. A method according to claim 14, wherein step (d) is executed methodically and systematically with a large number of members of the adjoiner species.

18. A method according to claim 14, 15 or 17, wherein said test species is able to reproduce in or on the adjoiner species.

19. A method according to claim 14, 15 or 17, wherein step (a) comprises the step of:

(d) selecting the test species from among test species that are or were attached or internal to a member of the adjoiner species that has undergone said desirable change in the behavior pattern.

20. A method according to claim 14, 15 or 17, wherein step (a) comprises the step of:

(d) selecting the test species from among test species that are or were attached or internal to a member of the adjoiner species that has undergone at least a partial desirable change in the behavior pattern.

21. A method according to claim 14, 15 or 17, wherein step (a) comprises the step of:

(f) selecting the test species from among test species that are or were attached or internal to a member of the adjoiner species that has undergone at least a temporary desirable change in the behavior pattern.

22. A method according to claim 14, 15 or 17, wherein the adjoiner species is the human species.

23. A method according to claim 14, 15 or 17, wherein the adjoiner species has a near-human species genetic composition.

24. A method according to claim 14, 15 or 17, further comprising prior to step (a) the step of:

(f) identifying the test species as a symbiont of the adjoiner species when the test species had not been known to be a symbiont of the adjoiner species.

25. A product for causing a desirable change in a behavior pattern of some members of an adjoiner species from an initial behavior pattern to a desired behavior pattern, comprising an ingredient that includes, is based upon, is derived from, or is equivalent to a carrier-member of a test species that is a symbiont of the adjoiner species and has been identified as possibly causing the desirable change in the behavior pattern of some members of the adjoiner species.

26. A process for making a product that causes a desirable change in a behavior pattern of some members of an adjoiner species from an initial behavior pattern to a desired behavior pattern, the process comprising the step of:

(a) including within said product an ingredient that includes, is based upon, is derived from, or is equivalent to a carrier-member of a test species that is a symbiont of the adjoiner species and has been identified as possibly causing the desirable change in the behavior pattern of some members of the adjoiner species.

27. A method of causing a desirable change in a behavior pattern of a subject member of an adjoiner species from an initial behavior pattern to a desired behavior pattern, the method comprising the step of:

(a) introducing to the subject member of the adjoiner species a product including an ingredient that includes, is based upon, is derived from, or is equivalent to a carrier-member of a test species that is a symbiont of the adjoiner species and has been identified as possibly causing the desirable change in the behavior pattern of some members of the adjoiner species.

28. A method according to claim 27, further comprising prior to step (a) the step of:

(b) introducing an antibiotic to the subject member of the adjoiner species.

29. A method of identifying a component of a carrier-member of a test species that is a symbiont of an adjoiner species and has been identified as possibly causing a desirable change in a behavior pattern of at least one member of the adjoiner species from an initial behavior pattern to a desired behavior pattern, the method comprising the steps of:

(a) providing either (i) a sample of the identified carrier-member of the test species or (ii) a culture of the identified carrier-member of the test species;

(b) separating the identified carrier-member of the test species or the culture thereof into a plurality of components;

(c) introducing at least one of the separated components to at least one member of an adjoiner species that has the initial behavior pattern; and subsequently (d) collecting data that indicates that the at least one member of the adjoiner species has acquired the desired behavior pattern to thereby make said component identification.

30. A product for causing a desirable change in a behavior pattern of some members of an adjoiner species from an initial behavior pattern to a desired behavior pattern, comprising an ingredient that includes, is based upon, is derived from, or is equivalent to at least one component separated from a culture of a carrier-member of a test species that is a symbiont of the adjoiner species, wherein the at least one component has been identified as possibly causing the desirable change in the behavior pattern of some members of the adjoiner species.

31. A process for making a product that causes a desirable change in a behavior pattern of some members of an adjoiner species from an initial behavior pattern to a desired behavior pattern, comprising the step of:
- (a) including within said product an ingredient that includes, is based upon, is derived from, or is equivalent to at least one component separated from a culture of a carrier-member of a test species that is a symbiont of the adjoiner species, wherein the at least one component has been identified as possibly causing the desirable change in the behavior pattern of some members of the adjoiner species.

32. A method of causing a desirable change in a behavior pattern of a subject member of an adjoiner species from an initial behavior pattern to a desired behavior pattern, wherein the method comprising the step of:
- (b) introducing to the subject member of the adjoiner species a product including an ingredient that includes, is based upon, is derived from, or is equivalent to at least one component separated from a culture of a carrier-member of a test species that is a symbiont of the adjoiner species, wherein the at least one component has been identified as possibly causing the desirable change in the behavior pattern of some members of the adjoiner species.

* * * * *